United States Patent [19]

Navarro Torres et al.

[11] Patent Number: 5,719,282
[45] Date of Patent: Feb. 17, 1998

[54] 1,4-BIS(AMINO) BENZO[G]PHTHALAZINE COMPOUNDS

[75] Inventors: Pilar Navarro Torres; Lucrecia Campayo Pérez; José Antonio Escario Garcia Trevijano, all of Madrid; Ismael Alvarez Rodriguez, Alcobendas, all of Spain

[73] Assignee: Consejo Superior De Investigaciones Cientificas, Madrid, Spain

[21] Appl. No.: 438,618

[22] Filed: May 10, 1995

Related U.S. Application Data

[63] Continuation of Ser. No. 656,150, filed as PCT/ES90/00016, May 14, 1990, abandoned.

[30] Foreign Application Priority Data

May 19, 1989 [ES] Spain ........................ 8901705

[51] Int. Cl.[6] .................. C07D 237/26; C07D 237/34; A61K 31/50
[52] U.S. Cl. ........................ 544/234; 544/115; 514/232.8; 514/248
[58] Field of Search ..................... 544/234, 115; 514/248, 232.8

[56] References Cited

U.S. PATENT DOCUMENTS

| | | | |
|---|---|---|---|
| 4,399,151 | 8/1983 | Sjoerdsma et al. | 424/319 |
| 4,992,433 | 2/1991 | Stokbroekx et al. | 514/212 |
| 5,162,320 | 11/1992 | Gandolfi et al. | 514/248 |

FOREIGN PATENT DOCUMENTS 533464  8/1985  Spain.

OTHER PUBLICATIONS

Campayo, L. et al., "Synthesis and cytostatic activity of 1,4-bis-(alkylamino)benzo(g) phthalazines with complexing properties" European Journal of Medicinal Chemistry, Chimie Therapeutic vol. 21, No. 2 (1986), pp. 143-149.

Campayo, L. et al., "Protonation of 1,4,-Bis(alkylamino)benzo[g]phthalazine. Crystal structure of Di-(1, 4-bis-(3-methoxypropylamino)-3(2)H-benzo[g] phthalazinium) Tetrachloro-cobaltate Monohydrate" J. Chem. Soc. Perkins Trans. II (1987), pp. 569-573.

Campayo et al Chemical Abstracts, vol. 106 (1987) Columbus, Ohio, p. 477, No. 106:5067u.

Advanced Organic Chemistry by Jerry March (2nd Ed.) p. 377 (1977).

Primary Examiner—Emily Bernhardt
Attorney, Agent, or Firm—Darby & Darby

[57] ABSTRACT

The invention relates to new compounds derived from 1,4-bis(alkylamino)benzo[g]phthalazenes of formula (I) which are useful as anticancerous and antiparasitic agents.

8 Claims, No Drawings

1,4-BIS(AMINO) BENZO[G]PHTHALAZINE COMPOUNDS

This is a continuation of application Ser. No. 07/656,150, filed as PCT/ES90/00016, May 14, 1990, now abandoned.

The present invention provides novel compounds such as certain 1,4-bis(alkylamino)benzo[g]phthalazines which are useful as anticancer and antiparasitic agents.

Novel 1,4-bis(amino)benzo[g]phthalazine compounds

BACKGROUND OF THE INVENTION

Daunomycin and Adriamycin play an important role in the clinical treatment of malignant diseases (1). However, these drugs possess cardiotoxicity which was attributed to their aminosugar moiety (2). Many research efforts have been directed towards developing new DNA complexing agents in which the above mentioned side effects would be minimized. Attention has been directed to the anthraquinone and amino moieties of adriamycin as the most likely sites for its known intercalative binding to DNA. Therefore, various flat tricyclic aromatic systems with basic side chains instead of daunosamine have been obtained including ametantrone and mitoxantrone which exhibit intercalating properties and excellent antineoplasic activity with diminished side effects (3). As the quinone moiety of the above drugs may lead to lipid peroxidation and DNA lesions in cardiac tissue (4), other highly active amentantrone analogues of reduced quinonic character have been reported (5). With the above mentioned aim, we have previously reported a new synthetic procedure of 1,4-bis(alkylamino)benzo[g]phthalazines (6) whose aromatic system containing two of the four conjugated nitrogen atoms as part of the ring with other two in an exocyclic amino group, is easily protonated (7) and shows strong intercalating properties toward DNA (8).

We have found that some derivatives of the above mentioned system such as 1,4-bis[(dimethylamino)propylamino] benzo[g] phthalazine and 1,4-bis[(dimethylamino) propylamino]-6-methoxy-benzo[g]phthalazine were powerful cytostatic compounds (9). Now we have discovered that other new derivatives of 1,4-bis(amino)benzo[g] phthalazine not bearing basic nitrogen atoms linked to the terminal carbons of their alkylamino chains are also powerful cytostatic agents and show antitumoral and antiparasitic activities.

DESCRIPTION OF THE INVENTION

The present invention provides novel compounds of the formula I

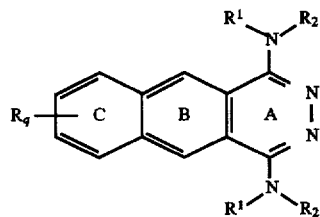

wherein,

The aryl moiety can be mono- or di-substituted at any feasible position(s) in the ring C (when q is 1 or 2 respectively) or it can be unsubstituted (when q is 0).

R is a lower alkyl, aryl, alkoxy, nitro, amino, alkylamino or acylamino group.

$R_1$ and $R_2$ are the same or different and are each, hydrogen atom, a lower alkyl, alkoxyalkyl, alkylaminoalkyl, aryl, aralkyl, cycloalkyl, cycloalkyl-alkylene, an heterocyclic ring linked to the nitrogens directly or by an alkylene chain, linear or branched, or $R_1$ and $R_2$ are taken together with the nitrogen to which they to form a attached are pyrrolidino, piperidino, morfolino, piperazino, 4-alkylpiperazino or 4-arylpiperazino group.

As used herein "lower alkyl" refers to a linear or branched alkyl group comprised of 1 to 6 carbon atoms.

The terms "alkoxyalkyl" and "alkylaminoalkyl" refer respectively to an alkoxy group or a monoalkylamino or dialkylamino group, attached to the nitrogen atoms by an alkylene group linear or branched. The term "aryl" refers to an aromatic group.

The term "aralkyl" refers to an aromatic ring attached to the nitrogen atoms by an alkylene bridge, linear or branched.

The term "cycloalkyl" refers to a saturated monocyclic hydrocarbon. The term cycloalkenyl refers to a partially unsaturated monocyclic hydrocarbon.

The term "heterocyclic ring" refers to an heterocyclic ring totally unsaturated, partially unsaturated or totally saturated.

Compounds of the formula I can be employed as free aromatic bases or as 1,4-bis(amino)benzo[g]phthalazinium salts, 2(3)methyl-1,4-bis(amino)benzo[g]phthalazinium salts or 2(3)ethyl-1,4-bis(amino)benzo[g]phthalazinium salts of the general formula II.

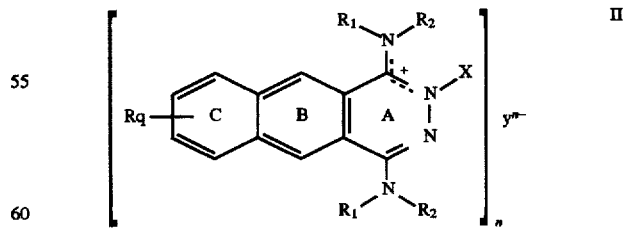

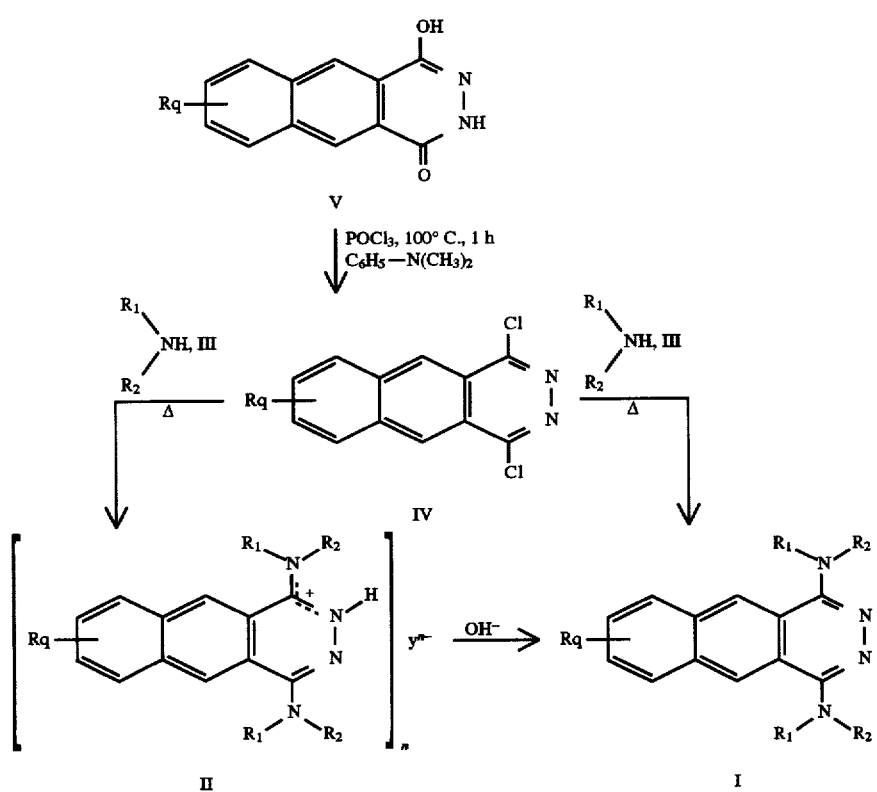

Scheme 1

*The Rq, R₁ and R₂ substituents are as previously defined wherein Rq, $R_1$ and $R_2$ are as defined above, n is 1 or 2, x is a hydrogen atom, a methyl or ethyl group and $y^{n-}$ is chloride, bromide, iodide, an oxoacid anion or an organic acid anion.

For example compounds of formula II prepared from compounds of formula I by treatment, with an acids such as hydrochloric, sulfuric, oxacid and the like or compounds prepared by addition of methyl halide are prepared or ethyl halide using conventional methods well known in the art.

In general, compounds of formula I may be prepared by a chemical procedure previously patented in Spain by us (6) according to the general synthetic route outlined in Scheme 1.

Compounds of formula I can be prepared by reacting the appropriately substituted benzo[g]phthalhydrazide V with phosphorous oxychloride and dimethylaniline to give the corresponding 1,4-dichloro-benzo[g]phthalazine IV, which is further reacted with the appropriate amine III, in an amount great enough to act as a reactant, solvent and an aacid cceptor to give the corresponding 1,4-bis(amino)-benzo[g]phthalazine compound.

From the reaction mixture the expected free base of formula I or its monohydrochloride of formula II it can be obtained. Treatment of the latter in basic medium affords the corresponding free base of formula I.

The following examples serve to illustrate the synthetic procedures to make compounds of the formula I according to the procedure outlined in Scheme 1. These examples are intented to be illustrative only and are not intented to limit the invention in any way.

EXAMPLE 1

1,4-bis(n-butylamine)benzo[g]phthalazine I (q=0; R=H; $R_1$=H; $R_2$=—$(CH_2)_3CH_3$ A mixture of 1,4-dichlorobenzo[g]phthalazine (9.23 mmol) and n-butylamine (20 mL) was heated in an autoclave at 130° C. for 12 h. After cooling to room temperature, the excess n-butylamine was evaporated to dryness under vacuum. The residue was extracted with chloroform and the resulting solution treated with an 5% aqueous solution of sodium hydroxide (100 mL). After the chloroform layer was separated and the organic solvent removed, the residue was purified by flash chromatography on silica gel Merck (200–400 mesh) using a mixture of n-hexane, ethyl acetate, methanol (v/v 1:1:0.3) as eluent. Removal of solvents from the fraction of Rf=0.11 afforded a yellow solid which was dissolved in chloroform and filtered through a column of basic aluminium oxide Merck. Removal of the chloroform to dryness afforded 1.1 gr (R=37%) of 1,4-bis(n-butylamine) benzo[g]phthalazine. m.p. 177°–179° C. having the following physical properties: IR(KBr) $v_{max}$ 3300, 3050, 2950, 2910, 2850, 1620, 1495, 1425, 1360, 1220, 1140, 880, 745, 675 cm⁻¹. ¹H NMR (DMSO-$d_6$) δ, 8.81 (s, 2H, $H_5$ and $H_{10}$); 8.10 (m, 2H, $H_6$ and $H_9$); 7.68 (m, 2H, $H_7$ and $H_8$), 6.44[m, 2H, NH (disappears with $D_2O$)]; 3.44 (t, 4H, 1'-$CH_2$-N), 1.69 (m, 4H, 2'-$CH_2$); 1.42 (m, 4H, 3'-$CH_2$), 0.94 (t, 6H, 4'-C$H_3$) ppm.

MS (m/z): 323 (M⁺+1.17) 322 (M⁺, 61) 279 (100).

Analysis: Calcd for $C_{20}H_{26}N_4$: C, 74.49 H, 8.12 N, 17.37 Found: C, 74.78 H, 7.96 N, 17.31

EXAMPLE 2

1,4-bis(n-butylamino)benzo[g]phthalazine monohydrochloride II [q=0; R=H; $R_1$=H; $R_2$=($CH_2$)$_3CH_3$, n=1, X=H; Y=Cl]

A mixture of 1,4-dichlorobenzo[g]phthalazine (9.23 mmol) and n-butylamine (20 mL) was heated in an autoclave at 130° C. for 12 h. After cooling to room temperature, the excess of n-butyl amine was evaporated to dryness under vacuum. When the residue was treated with acetone (100 mL) a yellow solid was formed. After being filtered off and dried it afforded 1.87 g (55% yield) of 1,4-bis(n-butylamino) benzo[g]phthalazine monohydrochloride. m.p. 195°–197° C.

IR (KBr) $v_{max}$ 3320–2600 (3240, 3100, 3000, 2940, 2920, 2850), 1625, 1575, 1545, 1425, 1360, 1325, 1155, 1025, 900, 760, 678 $cm^{-1}$.

$^1$H NMR (DMSO-$d_6$) δ, 9.38 (s, 2H, $H_5$ and $H_{10}$), 8.22 (m, 2H, $H_6$ and $H_9$), 7.88 (m, 2H, $H_7$ and $H_8$), 3.43 (m, 4H, 1'-C$\underline{H}_2$-N), 1.93–1.13 (m. broad, 8H, 2'-C$\underline{H}_2$ and 3'-C$\underline{H}_2$), 0.93 (t, 6H, 4'-C$\underline{H}_3$) ppm.

Analysis Calcd. for $C_{20}H_{26}N_4 \cdot 1$ HCl. 0.5 $H_2O$: C, 65.31 H, 7.62 N, 15.24 Cl, 9.64 Found: C, 65.07 H, 7.73 N, 15.02 Cl, 9.54

EXAMPLE 3

Preparation of 1,4-bis(n-butylamino)-6-methoxy-benzo[g]phthalazine I [q=1; R=$OCH_3$ (at C-6); $R_1$= H; $R_2$=($CH_2$)$_3CH_3$]

A mixture of 1,4-dichloro-6-methoxybenzo[g]phthalazine (3.94 mmol) and n-butylamine (25 mL) was treated in an autoclave at 130° C. for 6 h. After cooling to room temperature, the excess n-butylamine was evaporated to dryness under vacuum and the residue was extracted with chloroform (2×50 mL). The resulting extracts were concentrated and purified by flash chromatography on silica gel 60 Merck (200–400 mesh), using a mixture of chloroform, benzene, methanol (v/v, 1:0.5:0.2) as eluent. The removal of the solvents from the fraction of Rf=0.11 afforded 0.67 g (48%) of 1,4-bis(n-butylamino)-6-methoxy-benzo[g] phthalazine as a brown solid, melting at 178°–180° C., which shows the following physical properties:

IR (KBr) $v_{max}$ 3280, 3050, 2950, 2900, 2850, 1645, 1630, 1560, 1500, 1450, 1360, 1255, 1140, 1020, 790, 740 $cm^{-1}$.

$^1$H NMR (DMSO-$d_6$)δ, 9.06 (s, 1H, $H_5$); 8.83 (s, 1H, $H_{10}$), 7.64 (m, 2H, $H_8$ and $H_9$), 7.12 (m, 1H, $H_7$), 6.9–7.5 [m, 2H, NH (disappears with $D_2O$)], 4.05 (s, 3H, C$\underline{H}_3$O), 3.52–3.42 (m, 4H, 1'-C$\underline{H}_2$-N), 1.70 (m, 4H, 2'-C$\underline{H}_2$), 1.43 (m, 4H, 3'-C$\underline{H}_2$), 0.95 (t, 6H, 4'-C$\underline{H}_3$) ppm.

MS (m/z): 353 ($M^+$+1,23), 352 ($M^+$, 67) 309 (100).

Analysis Calcd. for $C_{21}H_{28}N_4O \cdot 1$ MeOH. 0.2 $H_2O$ C, 68.11 H, 8.35 N, 14.45 Found: C, 67.93 H, 8.43 N, 14.67

By following procedures analogous to that described above, the following 1,4-bis-benzo[g]phthalazines can be prepared:

1,4-bis(n-butylamino)-6-dimethylamino-benzo[g] phthalazine
1,4-bis(n-propylamino)benzo[g]phthalazine
1,4-bis(n-propylamino)-6-methoxy-benzo[g]phthalazine
1,4-bis(n-propylamino)-6-dimethylamino-benzo[g] phthalazine
1,4-bis(ethylamino)benzo[g]phthalazine
1,4-bis(ethylamino)-6-methoxy-benzo[g]phthalazine
1,4-bis(ethylamino)-6-dimethylamino-benzo[g]phthalazine
1,4-bis(methylamino)benzo[g]phthalazine
1,4-bis(methylamino)-6-methoxy-benzo[g]phthalazine
1,4-bis(methylamino)-6-dimethylamino-benzo[g] phthalazine
1,4-bis(amino)benzo[g]phthalazine
1,4-bis(amino)-6-methoxy-benzo[g]phthalazine
1,4-bis(amino)-6-dimethylamino-benzo[g]phthalazine The starting materials for the above reaction Scheme 1, i.e., the appropriately substituted 2,3-dihydrobenzo[g] phthalazine-1,4-diones (V) and their corresponding 1,4-dichloroderivatives (IV), are readily obtained through the use of commonly available reagents modified if required through standard synthetic schemes, procedures and techniques well known and appreciated by those of ordinary skill in the art.

For example, the starting 2,3-dihydrobenzo[g] phthalazine-1,4-diones V for compounds of formula I wherein q=0 or 1 and R is an hydrogen atom, $NO_2$, $OCH_3$ or $(CH_3)_2N$ groups substituted at C-6 can be prepared by procedures analogous to that described by P. Navarro et al. (10, 11). The appropriate 1,4-dichlorobenzo[g]phthalazines IV intermediates for compounds of formula I wherein q=0 or 1 and R is H, $NO_2$, $OCH_3$ or $N(CH_3)_2$ group can be prepared by procedures analogous to that described by P. Navarro et al. (9,10).

In another embodiment, the compounds of formula I of this invention exhibit antitumor activity "in vitro" and "in vivo" as well as an excellent tripanosomicide and trichomonacide activity "in vitro".

It is generally believed that there is a correlation between compounds which exhibit antiparasitic activity "in vitro" and the medical effect of being useful in treating parasitic infection in a patient suffering therefrom.

The following compound:

1,4-bis(n-butylamino)benzo[g]phthalazine (BBPh) is a particularly preferred embodiment of the present invention as is shown by the following Experiments:

Experiment 1: ANTITUMORAL ACTIVITY

I. "In vitro" effects:

The cytostatic and cytocidal activity of BBPh has been evaluated employing HeLa cell lines (from a human uterine cervix carcinoma), ADLD-clon (from a human malignant melanoma) and a semicontinuos LMMB cell line (from normal human tonsilar fibroblasts).

In order to perform both "in vitro" and "in vivo" experiments a concentrated stock solution of BBPh in dimethyl sulfoxide (DMSO) was prepared. From it increasing diluted solutions in McCoy's R5aI grown medium supplemented with 5% human serum, 5% calf serum, 5% fetal bovine serum, 100 IU/mL penicillin, 100 ug/mL streptomycin and 16 ug/mL gentamycin were obtained.

Serial dilutions of BBPh and the solvent were assayed in cultures seeded 24 hours before on 96-well "Microtiter" plates. The seeding was carried out by depositing 200 μL of cell suspension in growth medium in each well, adjusted to $3\times10^5$/mL HeLa cells, $9\times10^5$/mL ADLD-clon cells or $4\times10^5$/mL LMMB cells.

The plates with different concentrations of BBPh and control solutions were incubated at 37° C. in an air atmosphere containing 95% humidity containing 5% $CO_2$.

Then the plates were fixed and stained to estimate the effects of BBPh under the conditions described by Alvarez (1986) (11) taking Adriamycin as antitumor compound of reference. Under the above mentioned conditions, the 50 percent inhibitory dose ($ID_{50}$) or concentration producing the death or growth inhibition of 50% of the cells of Adriamycin and BBPh were very close as indicated below:

| Cell Cultures | $ID_{50}$ (μg/mL) | |
|---|---|---|
| | BBPh | Adriamycin |
| HeLa | 0.67 | 0.33 |
| ADLD-clon | 0.67 | 0.33 |
| LMMB | 1.08 | 0.07 |

It was also observed that the morphology adopted by the cells exposed to inhibitory doses is clearly different for cells treated with Adriamycin or BBPh. Adriamycin inhibited cells showing very big nuclei, indicating that growth inhibition is produced after the S phase has taken place. However, cells inhibited by BBPh show always small nuclei possibly because the stop in growth is produced before the S phase.

It is interesting to note that BBPh is slightly less toxic "in vitro" for normal LMMB cells than for HeLa and ADLD-clon neoplastic cells contrary to what happens in the case of Adriamycin, which shows a toxicity slightly higher on normal than on the neoplastic cells used in these assays.

II. "In vivo" effects

Five groups of six 2-month male swiss mice weighing 25 grams were arranged for treatment. Each animal received a transplant of $10^5$ Ehrlich ascites cancer cells by the subcutaneous route in the interscapular region. Fourteen days later, when the tumors were evident and measured more than 3 millimeter in diameter, the animals were submitted to the different treatments.

Group 1 received a first intraperitoneal dose of 300 μL of DMSO followed by equal an subcutaneous doses, the next three consecutive days.

Group 2 received a single intraperitoneal dose of 100 μg of BBPh solubilized in 300 μL of DMSO, followed by an equal subcutaneous doses the next three consecutive days.

Group 3 received a single intraperitoneal dose of 500 μg of BBPh in 300 μL of DMSO.

Group 4 received a single intraperitoneal dose of 1.000 μg of BBPh in 300 μL of DMSO.

Group 5 received a single subcutaneous dose of 4.000 μg BBPh in an oily solution.

Tables 1 and 2 summarize the main data related to the evolution of the tumors and surviving animals of each group.

TABLE 1

EFFECT OF BBPh ON TUMOR DEVELOPMENT USING DMSO AND OIL AS SOLVENTS

| MOUSE GROUP | TREATMENT | T/S[a] | GI-30[b] | ANIMAL N° | TUMOR SIZE (mm) | | | SURVIVAL (DAYS) | |
|---|---|---|---|---|---|---|---|---|---|
| | | | | | ST[c] | 45D[d] | 45-ST[e] | IST[f] | MST[g] |
| 1 | DMSO-TREATED CONTROL | 4/4 | 0/4 | 1 | 3 | 28 | 25 | 58 | 59 |
| | 1 × 300 μL i.p. | | | 2 | 3 | 34 | 31 | 64 | |
| | 3 × 300 μL s.c. | | | 3 | 4 | 37 | 33 | 58 | |
| | | | | 4 | 11 | 29 | 18 | 58 | |
| 2 | BBPh in DMSO | 6/5 | 2/5 | 1 | 3 | 3 | 0 | 135 | 84 |
| | 1 × 0.1 mg in 300 μL i.p. | | | 2 | 9 | 20 | 11 | 78 | |
| | 3 × 0.1 mg in 300 μL s.c. | | | 3 | 9 | 22 | 13 | 78 | |
| | | | | 4 | 9 | 25 | 16 | 78 | |
| | | | | 5 | 11 | 20 | 9 | 53 | |
| 3 | BBPh in DMSO | 6/2 | 1/2 | 1 | 3 | 23 | 20 | 66 | 95 |
| | 1 × 0.5 mg in 300 μL i.p. | | | 2 | 9 | 10 | 1 | 125 | |
| 4 | BBPh in DMSO | 6/0 | | — | — | — | — | — | — |
| | 1 × 1.0 mg in 300 μL i.p. | | | | | | | | |
| 5 | BBPh IN OILY SOLUTION | 5/5 | 3/5 | 1 | 9 | 9 | 0 | 131 | 86 |
| | 1 × 4.0 mg S.C. | | | 2 | 9 | 18 | 9 | 64 | |
| | | | | 3 | 9 | 19 | 10 | 46 | |
| | | | | 4 | 9 | 34 | 25 | 64 | |
| | | | | 5 | 11 | 15 | 4 | 125 | |

(a) Ratio between the number of available animals treated and the number of animals surviving to acute toxicity effects
(b) Tumor growth stop after 30 days
(c) Tumor size when the treatment was started
(d) Tumor size 45 days after the treatment was started
(e) Size difference between 45D and ST
(f) Individual survival time in days
(g) Median survival time in days

TABLE 2

ANTITUMORAL ACTIVITY OF BBPh ON EHRLICH ASCITES CANCER CELLS USING DMSO AS SOLVENT

| Drug | Overal Dose (mg/Kg) | TST (days) | T/C* (%) | Toxic death |
|---|---|---|---|---|
| Control[a] (DMSO-treated) | — | 59 | — | 0/6 |
| BBPh | 16[b] | 84 | 142[f] | 1/6 |
| BBPh | 20[c] | 96 | 161[f] | 4/6 |
| BBPh | 40[d] | 1 | Toxic | 6/6 |

[a] A first i.p. dose of 0.3 mL of DMSO followed by similar s.c. doses the next three consecutive days
[b] A first i.p. dose of 0.1 mg BBPh solubilized in 0.3 mL of DMSO, followed by similar s.c. doses the next three consecutive days
[c] A single i.p. dose of 0.5 mg BBPh in 0.3 mL of DMSO
[d] A single i.p. dose of 1.0 mg BBPh in 0.3 mL of DMSO
*T/C (%) = Median survival of treated animals (T)/Median survival time of control animals (C) × 100. (A compound may be considered active when T/C % value is >125%)

The data gathered in Table 1 indicate that BBPh produce a clear inhibition of tumor growth either using DMSO as solvent (groups 2 and 3) or oily solutions (group 5). Using DMSO as solvent via intraperitoneal (i.p.) in a single dose of 20 mg/Kg the BBPh was toxic. However its 50 percent lethal dose ($LD_{50}$=12 mg/Kg) is much lower than those exhibited by many clinical drugs actually used in the treatment of malignant diseases such as Actinomicin D ($LD_{50}$=0.095 mg/Kg), Vincristine ($LD_{50}$=4.5 mg/Kg), Dichloroplatinum II ($LD_{50}$=8.9 mg/Kg) or Daunomycin ($LD_{50}$=9.2 mg/Kg) (12).

Besides when a DMSO solution of BBPh (0.1 mg in 0.3 mL of DMSO) is administered in four consecutive days using a mixed treatment (one dose i.p. followed by three doses s.c.) the toxic deaths are drastically reduced (T/S=6/5) and the median survival time of the treated animals (group 2: MST=84 days) is considerable higher than the survival time exhibited by the DMSO-treated control (group 1: MST=59 days).

Furthermore it is interesting to observe that any animal belonging to group 5 which was treated with an oily solution of BBPh administered in a single and high s.c. dose of 160 mg/kg it does not suffer toxic death (T/S=5/5) and the median survival time was 86 days (table 1).

Considering the above mentioned results together with the T/C % values indicated in table 2 we can assert that BBPh shows a clear antineoplasic activity in vivo against Ehrlich ascites cancer cells.

Experiment 2. TRYPANOSOMICIDE ACTIVITY

Human Chagas' disease caused by *Trypanosoma cruzi* affects nearly 12 millions of people in the world and shows a considerable mortality rate associated with new infections. In spite of this until now there is not any effective treatment of the above mentioned disease and only Nifurtimox and Benzonidazole are used with moderate success (13).

Although *Trypanosoma cruzi* is usually transmitted by blood sucking vectors, blood transfusion is also an important source of infection in urban areas of endemic zones (14). Consequently, there is an urgent need for the development of new effective medicaments for the direct treatment of Chagas' disease treatment as well as for the prevention of its transmission by blood transfusions (15).

Some anticancer drugs such as mitomycin C and antinomycin D which interact with nucleic acids have shown activity against *Trypanosoma cruzi* (16). Furthermore the trypanosomicide activity exhibited in general by intercalating agents such as phenanthridinium salts (i.e. ethidium bromide) has been related to the quaternization of the phenanthridine nucleous (17). Following a similar behaviour the 1,4-bis(butylamino)benzo[g]phthalazine (BBPh) which is able to form 1,4-bis(butylamino)benzo[g]phthalazinium cations at physiological PH (PKa of BBPh=8.6) and is a potential intercalating agent has shown both, antineoplasic and trypanosomicide activities.

"In vitro" effects:

The Y. strain of *T. cruzi* used in this experiment was isolated in 1953 from an infected human and it is defined as "depended cell" strain due to its affinity for invading reticule endothelial cells. It is characterized by the abundance of slender blood forms and by its high virulence in white mice.

In order to evaluate the activity of BBPh, NMRI mice were inoculated with *T. Cruzi* and exanguinated after 7–10 days by cardiac punture using heparin as an anticoagulant. The infected blood was mixed with normal blood and 0.5 mL of the resulting mixture containing a parasite density of 500.000/mL calculated by using the Brener' Method (18), was mixed with 0.5 mL of a solution of BBPh in saline phosphate buffer (PBS) containing 16% ethylene glycol. Five different doses of 1000, 500, 250, 125 and 75 ug/mL of BBPh were assayed using three identical tubes for each of them taking as reference an additional tubes containing Ct control (0.5 mL of infected blood and 0.5 mL of PBS) and Cd control (0.5 mL of infected blood and 0.5 mL of PBS solution containing 16% of diethylene glycol).

After the above samples were kept in the refrigerator at 4° C. and shaked for an incubation period of 24 h, the parasites were again counted.

Under the above mentioned conditions all the samples treated with BBPh showed negative parasitemia (Table 3).

TABLE 3

Trypanosomicide acitivity of BBPh "in vitro".
Examination of NMRI mice blood infected with *T. cruzi* (500.000/mL) after be treated with BBPh and incubated 24 h at 4° C.

| | Cd[a] | Ct[b] | BBPh (µg/mL) | | | | |
|---|---|---|---|---|---|---|---|
| | | | 1000 | 500 | 250 | 125 | 75 |
| N° Tryp/mL | 298 | 247 | 0 | 0 | 0 | 0 | 0 | a) 0.5 mL of infected blood and 0.5 mL of a phosphate buffer saline (BBS) solution containing 16% of diethylene glycol b) 0.5 mL of infected blood and 0.5 mL of PBS)

c) 0.5 mL of infected blood and 0.5 mL of a solution of BBPh in PBS containing 16% of ethylene glycol

Experiment 3: TRICHOMONACIDE ACTIVITY

"In vitro" effects:

The cultures of the strains of *Trichomonas vaginalis* (Stain G) used as experimental model were grown in Diamond Medium (TYM) without agar (100.000 organisms/mL). The 1,4-bis(butylamino)benzo[g]phthalazine (BBPh) was added to the cultures at the different preestablished doses 6 h after reseeding (hour 0); counting was made after 24 h and 48 h of contact between the compound and protozoa at 37° C. Minimal inhibition concentration (MIC) and Minimal cytocidal concentration (MCC) were established in accordance with the definitions proposed by Escario et al. (19). The resulting data are as follows:

| Compound | Trichomonacidal activity (μg/mL) | |
| --- | --- | --- |
| | MIC | MCC |
| Metronidazole | 4–8 | 8 |
| BBPh | 5–10 | 10–25 |

From the above values it can be observed that the trichomonacide activity of BBPh is very close to the activity exhibited by metronidazole which was taken as reference in this experiment.

REFERENCES AND NOTES (1) F. Arcamone "Doxorubicin Anticancer Antibiotics", Academic Press, New York (1981)

(2) R. H. Adamson, *Cancer Chemother. Rep.*, 1974, 58, 293.

(3) I. E. Smith, *Cancer Treat Rev.*, 1983, 10, 103.

(4) J. W. Jown, S. M. Sondhi, S. B. Mandal and J. Murphy, *J. Org. Chem.*, 1982, 47, 4304.

(5) H. D. H. Showalter, J. L. Johnson, L. M. Werbel, W. R. Leopold, R. C. Jackson, E. F. Elslager, *J. Med. Chem.*, 1984, 27, 255.

(6) L. Campayo and P. Navarro. Spanish Patent n° 533464 (1984)

(7) L. Campayo, F. H. Cano, C. Foces-Foces and P. Navarro, *J. Chem. Soc., Perkin Trans II*, 1987, 569–573

(8) E. Giralt, M. Pons, L. Campayo and P. Navarro, Unpublished results.

(9) L. Campayo and P. Navarro, *Eur. J. Med. Chem. Chem. Ther.* 1986, 21, 143–149.

(10) L. Campayo, B. Jiménez, T. Manzano, P. Navarro, *Synthesis*, 1985, 197–200.

(11) I. Alvarez, "Trends in Cancer Research S-3", Ed. Servicio Editorial de la Universidad del País Vasco, 1986, p 199–218

(12) F. M. Shabel, D. P. Griswold, T. H. Corbett, W. R. Laster, J. G. Mayo and H. H. Lloyd, "Methods in Cancer Research", vol 17, Cancer Drug Developpment Part B. Ed. by V. T. Devita and H. Bush, New York, Academic Press IN. 1979, p 3–51.

(13) L. S. Filardi, Z. Brener, *Trans. R. Soc. Trop. Med. Hyg.*, 81 (5), 755–9 (1987).

(14) H. M. Souza, C. A. Morais, J. R. Mineo. *Rev. da Soc. Brasil de Med. Trop.*, 1985, 18 (1), 11–15.

(15) D. J. Hammond, J. Hogg, W. E. Gutteridge, *Exp. Parasitol.*, 1985, 60, 32–42.

(16) J. F. Fernandez, M. Halsman and O. Castellani, *Nature* (London), 1965, 207, 1004–1005.

(17) W. J. Ross in "Chemotherapy of Trypanosomiasis Protozoan Diseases" in "Burger's Medicinal Chemistry" Part II, Ed. by M. E. Wolf, John Willey and Sons Inc. New York. p. 439 (1979).

(18) Z. Brener. *Adv. in Pharmacol. and Chemother.*, 1975, 13, 1–44.

(19) J. A. Escario, A. Sanchez-Souza, C. Gómez-Criado, M. L. Jiménez, E. A. Fernández-Jorg and F. Baquero. *Ann. Inst. Pasteur,* 1985, 136A, 371.

We claim:

1. 1,4-bis(n-butylamino)benzo[g]phthalazine.

2. 1,4-bis(n-butylamino)-3(2)H-benzo[g]phthalazinium chloride.

3. 1,4-bis(n-butylamino)-6-methoxy-benzo[g]phthalazine.

4. 1,4-bis(n-butylamino)-6-methoxy-benzo[g]phthalazinium chloride.

5. 1,4-bis(n-propylamino)-benzo[g]phthalazine.

6. 1,4-bis(n-propylamino)-3(2)H-benzo[g]phthalazinium chloride.

7. 1,4-bis(n-propylamino)-6-methoxy-benzo[g]phthalazine.

8. 1,4-bis(n-propylamino)-6-methoxy-3(2)H-benzo[g]phthalazinium chloride.

* * * * *